United States Patent [19]

Kiske et al.

[11] Patent Number: 4,909,246
[45] Date of Patent: Mar. 20, 1990

[54] RESPIRATOR WITH MULTIPLE INSPIRATORY STROKES

[75] Inventors: Siegfried Kiske, Gross Gronau; Erik Schwanbom; Ernst-Guenter Scharmer, both of Luebeck, all of Fed. Rep. of Germany

[73] Assignee: Drägerwerk AG, Lübeck, Fed. Rep. of Germany

[21] Appl. No.: 343,789

[22] Filed: Apr. 26, 1989

[30] Foreign Application Priority Data

Jun. 14, 1988 [DE] Fed. Rep. of Germany ....... 3820165

[51] Int. Cl.$^4$ ............................................. A62B 7/00
[52] U.S. Cl. .......................... 128/205.14; 128/205.17
[58] Field of Search ...................... 128/204.28, 205.13, 128/205.14, 205.17, 204.21, 204.18, 205.24, 205.15, 203.14

[56] References Cited

U.S. PATENT DOCUMENTS

| | | | |
|---|---|---|---|
| 3,200,816 | 8/1965 | Bartlett, Jr. ..................... | 128/205.13 |
| 3,844,280 | 10/1974 | Smythe et al. .................. | 128/205.13 |
| 3,921,628 | 11/1975 | Smythe et al. .................. | 128/205.13 |
| 3,985,131 | 10/1976 | Buck et al. ...................... | 128/205.13 |
| 4,020,834 | 5/1977 | Bird ................................ | 128/205.14 |
| 4,141,354 | 2/1979 | Ismach ........................... | 128/204.28 |
| 4,197,843 | 4/1980 | Bird ................................ | 128/205.14 |
| 4,351,329 | 9/1982 | Ellestad et al. ................. | 128/205.14 |
| 4,459,982 | 7/1984 | Fry .................................. | 128/205.14 |
| 4,702,242 | 10/1987 | Broddner et al. .............. | 128/205.13 |
| 4,811,732 | 3/1989 | Hartung ......................... | 128/204.28 |

Primary Examiner—Eugene H. Eickholt
Attorney, Agent, or Firm—McGlew & Tuttle

[57] ABSTRACT

A respirator comprises a respiratory air circulation unit with an adjustable displacement volume and a respiratory air supply line and a respiratory system comprising an inspiration loop, an expiration loop and valve elements mounted in these loops. The valve elements are controllable by means of a control unit, so that small as well as large displacement volumes can be executed by means of a single circulation unit with the smallest space requirements possible. For this purpose the inspiration phase is divided into several sub-phases, during which the control unit controls the valve elements and the respiratory air circulation unit 4 so that several fillings of the adjustable displacement volume are supplied to the inspiration loop and only then is the expiration phase initiated. Thus the displacement volume of the circulation unit can be kept small. One or a few inspiration sub-phases are sufficient for the artificial respiration of infants and premature infants, while a multitude of sub-phases can be executed for the artificial respiration of adults with a large respiratory volume.

6 Claims, 1 Drawing Sheet

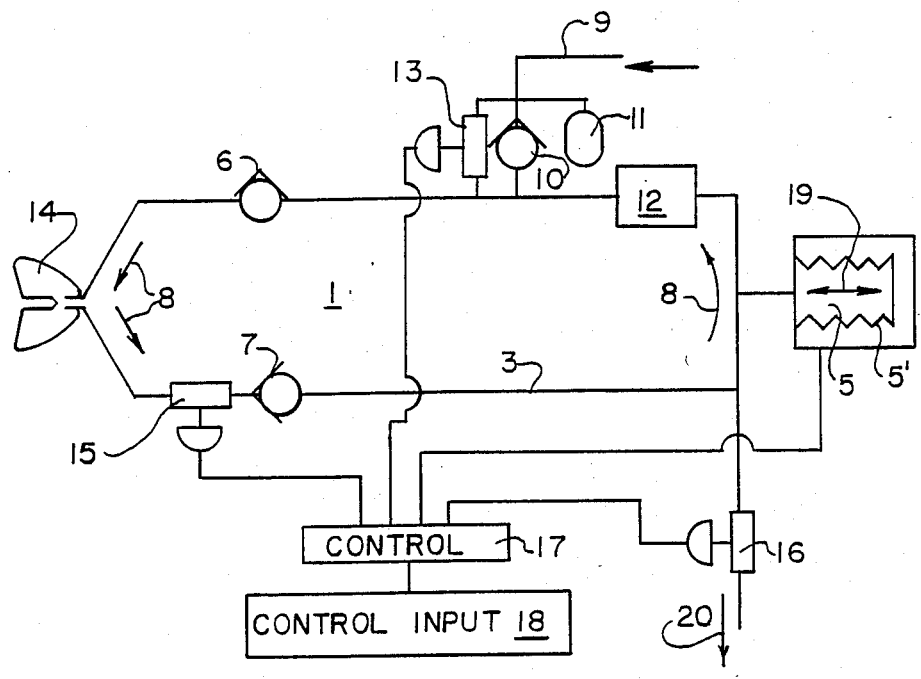

RESPIRATOR WITH MULTIPLE INSPIRATORY STROKES

BACKGROUND OF THE INVENTION

1. Field of the Invention

The invention relates, in general, to respirators and, in particular, to a new and useful respirator comprising a respiratory air circulation unit with an adjustable displacement volume and a respiratory air supply line and a respiratory system comprising an inspiration loop, an expiration loop and valve elements mounted in these loops and controllable by means of a control unit Such a respirator can be operated with a half-open or semi-open respiratory system without counter respiration or with a partially or completely closed respiratory system having counter respiration.

In known respirators with the option of counter respiration part of the expiration gas or all of the expiration gas is led back into the respiratory system and it is re-supplied to the patient during the following inspiration strokes of the respiratory air circulation unit once it is depleted of the exhaled $CO_2$ and enriched with a fresh gas and, in case of narcosis, with the required anesthetic. A half-open respiratory system is e.g. achieved when the fresh air supply flow is adjusted larger than or equal to the respiratory air volume per minute In this case the patient receives fresh respiratory air only and the used respiratory air is discharged through the discharge valve. The respiratory air circulation unit of the respirator takes in the respiratory air from the expiration loop and empties it into the inspiration loop. For this purpose the circulation unit is usually equipped with an adjustable volume, e.g. in the form of a bellows or a piston movable in a cylinder. Such a respirator is described in German Patent No. 34 34 908.

The amount Of the displacement volume required for the inspiration phase is determined by the displacement volume of the bellows or the piston-cylinder unit. Typical displacement volumes in adults are 0.5 to 1.5 liters, in extreme cases up to 2 liters, in premature infant and newborns, however, they are merely some 10 milliliters. A respirator whose circulation unit is calibrated for the large displacement volumes of adults can be used for a volume-constant artificial respiration of infants, premature infants or newborns only to a limited extent due to the inferior dosing accuracy for small displacement volumes. However, because of the small lungs of infants volume stability is indispensable.

Furthermore, a large displacement volume of up to 2 liters results in such a high unit-compliance that a volume-stable dosing of the small displacement volumes is jeopardized. The major space requirement of the known respirators, which have unnecessarily large displacement volumes when used for the artificial respiration of infants are regarded as negative. The option of equipping the respirator with special devices for the respiration with small displacement volumes, e.g. respectively smaller bellows or piston-cylinder units, does not result in improvements, as the respective scaling has to be changed also. Furthermore, this process incurs additional costs as piston-cylinder units or bellows of various sizes have to be stored.

SUMMARY OF THE INVENTION

The present invention provides a respirator constructed so that with the smallest space requirements possible small displacement volumes as well as large ones can be produced by the same circulation unit. According to this invention, this is effected in a respirator having an adjustable displacement volume which is divided into a plurality of partial volumes.

By means of the invention several inspiration sub-phases are executed by the circulation unit build up successively to form a complete inspiration phase. The displacement volume required for the inspiration is divided into several partial volumes. Due to this the adjustable displacement volume, e.g. a bellows, can have a fraction of the size of the displacement volume applied per respiration. Therefore it is possible to reduce the dimensions of the circulation unit so far that for the artificial respiration of infants with a displacement volume of e.g. 0.3 liters one filling and discharge into the inspiration loop is sufficient. For the artificial respiration of adults, however, the circulation unit executes three inspiration sub-phases in order to achieve the required displacement volume of 0.9 liters during the inspiration. In the artificial respiration of infants the minor unit-compliance due to the small displacement volume is a major advantage as the dosing accuracy of a volume-constant artificial respiration is increased.

The control of the supply valve and the discharge valve ensures that no respiratory air escapes from the expiration loop or flows back into the respiratory air supply line during the inspiration phase.

A further option is effected by the circulation unit, the supply valve and the expiration valve. The arrangement of a supply non-return valve parallel to the supply valve eliminates a separate control of the supply valve during the various inspiration sub-phases, as the filling from the supply line is effected through the opening supply non-return valve. The supply valve is opened only during the expiration.

It is advantageous to provide the expiration loop with a controllable discharge valve, which is opened only during the expiration phase. With a large supply of fresh air through the supply line and small displacement volumes the excess air can escape into the environment during expiration.

In order to achieve the required flexibility with regard to the size of the displacement volume, it is advantageous to determine the number of inspiration sub-phases by means of the control unit. Thus different displacement volumes can even be set while an artificial respiration takes place.

Furthermore it is advantageous to connect a gas storage container to the supply line, which is filled cyclically with the cleaned expiration gas and from which the circulation unit can take a partial amount for the inspiration loop. This is useful in particular when a small amount of fresh respiratory air or no air at all is supplied in the respiratory cycle.

Accordingly, is it an object of the invention to provide a respirator which includes a respiratory air circulation unit which has a movable stroke device with an adjustable displacement volume for supplying inspiration air to a respiratory air supply line which is connected to a respiratory system which comprises an inspiration loop and an expiration loop with valve elements mounted in each loop for controlling the flow therethrough and in which the valve elements are connected to a control unit which regulates the respiratory air circulation unit so that it executes at least two consecutive complete filling and emptying strokes during each inspiration before expiration takes place.

A further object of the invention is to provide a respirator which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawing and descriptive matter in which a preferred embodiment of the invention is illustrated.

BRIEF DESCRIPTION OF THE DRAWINGS

In the drawings:

The only FIGURE of the drawings is a schematic diagram of a respirator constructed in accordance with the invention.

DETAILED DESCRIPTION OF THE DRAWINGS

The respirator shown in the only drawing has a respiratory system 1 subdivided into an inspiration loop 2 and an expiration loop 3. The respiratory air is circulated as an adjustable displacement volume 5 by a respiratory air feed or circulation unit 4 with an expansion device such as a bellows 5' which is represented as a symbol. The direction of circulation in the respiratory system (1) is determined by an inspiration non-return valve 6 and an expiration non-return valve 7. The direction of flow is indicated by means of flow direction arrows 8. A respiratory air supply line 9 with a supply non-return valve 10 opens into the inspiration loop 2. Upstream of the supply non-return valve 10 a gas storage container 11 in the form of an elastic balloon is connected with the respiratory air supply line 9. Furthermore, a $CO_2$-absorber 12 is connected to the inspiration loop 2 between the respiratory air circulation unit 4 and the connection of the supply line 9. A controllable supply valve 13 is mounted parallel with regard to the supply non-return valve 10 The inspiration loop 2 and the expiration loop 3 supply a patient represented by a lung-symbol 14 with respiratory air. Upstream with regard to the expiration non-return valve 7 a controllable expiration valve 15 is provided and downstream with regard to the expiration non-return valve 7 a discharge valve 16, which is also controllable and which realizes the connection to the environment. A control unit 17 serves for the actuation of the controllable valves 13, 15, 16. The necessary control commands are transferrable to the control unit 17 by means of an input unit 18.

To execute an inspiration stroke, the respiratory air circulation unit 4 is induced to do a suction stroke by means of which the bellows 5 from the expiration loop 3 and the supply line 9 and/or the gas storage container 11 takes in the amount of respiratory air corresponding to its displacement volume. The supply valve 13, the expiration valve 15 and the discharge valve 16 are closed. Once the displacement volume of the bellows 5 is complete, the circulation unit 4 is switched over, so that the bellows 5 conveys its sucked-in displacement volume into the lungs 14 of the patient though the inspiration loop 2. Depending on setting of the input data in the input unit 18 the respiratory air circulation unit 4 is induced by the control unit 17 to execute several consecutive pumping strokes (shown by stroke arrows 19), which, as inspiration sub-phases, together form a complete inspiration phase. During these sub-phases respiratory air is again taken in from the respiratory air supply line 9 and the gas storage container Il and delivered into the inspiration loop 2. Once the inspiration is finished and the respective volume has blown into the lungs of the patient, all valves 13, 15, 16, but first of all the expiration valve, 15 are opened to allow for a pressure compensation in the respiratory system 1. Herein the bellows 5 and the gas storage container 11 are partially filled with expiration air and the excess is discharged into the environment 20 through the discharge valve 16. Once the exhalation phase is completed, the execution of the inspiration sub-phases commences again. Herein, depending on the requirements, a different number of sub-phases can be combined to an inspiration phase. The expiration air remaining in the respiratory system 1 during the expiration phase is depleted of its $CO_2$ while travelling through the $CO_2$-absorber 12. The used oxygen and in case of narcosis, the used anesthetic are supplied to the respiratory system 1 by means of the respiratory air supply line 9.

In a further variation, which is not shown, the supply non-return valve 10 is omitted, thus a connection between the supply line 9 and the inspiration loop 2 through the supply valve 13 is possible. In this embodiment the supply valve 13 has to be open during the process of filling the bellows 5 and it has to be closed while the bellows 5 empties its contents into the inspiration loop 2. The respective control is effected by the control unit 17. The remaining valves are controlled as described above.

While specific embodiments of the invention have been shown and described in detail to illustrate the application of the principles of the invention, it will be understood that the invention may be embodied otherwise without departing from such principles.

What is claimed is:

1. A respirator, comprising a respiratory air circulation unit having a movable stroke device with an adjustable displacement volume, a respiratory air supply line, a respiratory system connected to said air supply line comprising an inspiration loop, and an expiration loop, a valve element mounted in each of said inspiration loop and expiration loop, a control unit connected to each of said valve elements and to said respiratory air circulation unit for controlling the strokes of said unit, said unit having a volume capacity set to cause said unit stroke device to execute at least two consecutive complete filling and emptying strokes during each inspiration before expiration takes place.

2. A respirator according to claim 1, including a controllable supply valve in said supply line connected to said control unit, said valve elements including an expiration valve in said expiration loop, said stroke device including a movable member movable to effect a stroke to effect movement of air into said inspiration loop while said expiration valve is closed and whereas said stroke device executes a stroke which is emptied in a sub-phase into said inspiration loop while said supply valve is opened to effect filling of said stroke device, said supply valve being closed during the emptying phase of the stroke movement, so that for the execution of an expiration, the expiration valve and the supply valve are open.

3. A respirator according to claim 2, wherein said control unit controls said supply valve each supply line having a non-return return valve, said stroke device being movable so as to repeatedly take a filling from said supply line while said expiration valve and said supply valve are closed and wherein said stroke device empties as an inspiration flow through said inspiration loop into the patient and for the execution of an expiration, said expiration valve and said supply valve are open.

4. A respirator according to claim 3, wherein said expiration loop has a controllable discharge valve, which opens into the environment only during the expiration phase.

5. A respirator according to claim 4, wherein the number of the inspiration sub-phases serving the filling and emptying of the circulation stroke unit and said control unit acting on said inspiration and expiration valves can be determined through said control unit by means of an input unit connected to said control unit.

6. A respirator according to claim 5, including a gas storage container connected to said supply line and wherein said stroke device takes a partial filling from said storage container and a part of the respiratory air is returned during the expiration phase.

* * * * *